US010149825B2

(12) United States Patent
Jokinen et al.

(10) Patent No.: US 10,149,825 B2
(45) Date of Patent: Dec. 11, 2018

(54) METHOD FOR PREPARING ADJUSTABLY BIORESORBABLE SOL-GEL DERIVED $SIO_2$

(75) Inventors: Mika Jokinen, Turku (FI); Reeta Viitala, Turku (FI); Harry Jalonen, Turku (FI)

(73) Assignee: DelSiTech Oy, Turku (FI)

( * ) Notice: Subject to any disclaimer, the term of this patent is extended or adjusted under 35 U.S.C. 154(b) by 1622 days.

(21) Appl. No.: 10/590,451

(22) PCT Filed: Feb. 22, 2005

(86) PCT No.: PCT/FI2005/050046
§ 371 (c)(1),
(2), (4) Date: Aug. 24, 2006

(87) PCT Pub. No.: WO2005/082781

PCT Pub. Date: Sep. 9, 2005

(65) Prior Publication Data
US 2007/0196427 A1    Aug. 23, 2007

Related U.S. Application Data

(60) Provisional application No. 60/548,113, filed on Feb. 27, 2004.

(30) Foreign Application Priority Data

Feb. 27, 2004 (FI) ..................... 20040312

(51) Int. Cl.
| *C01B 33/14* | (2006.01) |
| *A61K 9/16* | (2006.01) |
| *A61K 9/00* | (2006.01) |
| *A61K 9/06* | (2006.01) |
| *A61K 9/14* | (2006.01) |
| *A61K 9/20* | (2006.01) |
| *C01B 33/16* | (2006.01) |
| *C03B 19/10* | (2006.01) |
| *C03B 19/12* | (2006.01) |
| *C03C 4/00* | (2006.01) |
| *C04B 35/14* | (2006.01) |
| *C04B 35/624* | (2006.01) |
| *C04B 35/626* | (2006.01) |
| *C04B 35/63* | (2006.01) |

(52) U.S. Cl.
CPC .......... *A61K 9/1611* (2013.01); *A61K 9/0024* (2013.01); *A61K 9/06* (2013.01); *A61K 9/143* (2013.01); *A61K 9/2009* (2013.01); *C01B 33/16* (2013.01); *C01B 33/163* (2013.01); *C01B 33/166* (2013.01); *C03B 19/1065* (2013.01); *C03B 19/12* (2013.01); *C03C 4/0007* (2013.01); *C03C 4/0014* (2013.01); *C04B 35/14* (2013.01); *C04B 35/624* (2013.01); *C04B 35/6264* (2013.01); *C04B 35/62605* (2013.01); *C04B 35/62655* (2013.01); *C04B 35/63* (2013.01); *C04B 2235/441* (2013.01)

(58) Field of Classification Search
CPC .... A61K 9/0024; A61K 9/143; A61K 9/1611; A61K 9/2009; A61K 9/06; C01B 33/16; C01B 33/163; C01B 33/166; C03B 19/1065; C03B 19/12; C03C 4/0007; C03C 4/0014; C04B 35/14; C04B 35/624; C04B 35/62605; C04B 35/6264; C04B 35/62655; C04B 35/63; C04B 2235/441
See application file for complete search history.

(56) References Cited

U.S. PATENT DOCUMENTS

| 5,200,334 A | 4/1993 | Dunn et al. .................. 435/182 |
| 5,468,558 A | 11/1995 | Derleth et al. .............. 428/402 |
| 6,632,412 B2 | 10/2003 | Peltola et al. ............... 423/338 |
| 7,112,339 B1 | 9/2006 | Ahola et al. ................. 424/484 |
| 2004/0120971 A1 | 6/2004 | Koskinen et al. ......... 424/204.1 |

FOREIGN PATENT DOCUMENTS

| JP | 6-157020 | 6/1994 |
| JP | 6-510268 | 11/1994 |
| WO | WO 92/20623 | 11/1992 |
| WO | WO 96/03117 | 2/1996 |

(Continued)

OTHER PUBLICATIONS

Danilyuk, et al, 1998. Supercritical extraction as a method for modifying the structure of supports and catalysts. Raeact. Kinet. Catal. Lett., vol. 63(1):193-199.*

Kortesuo, 2001. Sol-gel derived silica gel monoliths and microparticles as carrier in controlled drug delivery in tissue admininstration. Academic Disseration, Division of Biopharmaceutics and Pharmacokinetics, Department of Pharmacy, University of Helsinki.*

Rao and Pavarthy, 1993. Effect of gel paramters on monolithicity and density of silica aerogels. Journal of Materials Science, vol. 28:3021-3026.*

Siouffi, 2003. Silica gel-based monoliths prepared by the sol-gel method: facts and figures. Journal of Chromatography, vol. 1000: 801-818.*

(Continued)

Primary Examiner — David J Blanchard
Assistant Examiner — Thurman M Wheeler
(74) Attorney, Agent, or Firm — James C. Lydon

(57) ABSTRACT

A method for preparing a sol-gel derived $SiO_2$ having a very fast bioresorption rate where a sol-gel derived $SiO_2$ is prepared from a sol comprising water, an alkoxide or inorganic silicate and a lower alcohol using a mineral acid or a base as a catalyst and the sol is aged and dried. The method uses a pH from 1.5 to 2.5, a molar ratio of water to the alkoxide or inorganic silicate of 0.5 to 2.5, a molar ratio of alcohol to the alkoxide or inorganic silicate is ≥0.5; and the sol is either let to gel without induced changes of composition and without forced drying of the sol, or a change of composition is induced; and within a time of ≤30 minutes, from the induced change forced drying of the sol is carried out or initiated.

7 Claims, 4 Drawing Sheets

(56) References Cited

FOREIGN PATENT DOCUMENTS

WO     WO 97/45367     12/1997
WO     WO 00/50349     8/2000

OTHER PUBLICATIONS

Kortesuo, 2001. Sol-gel derived silica gel monoliths and microparticles as carrier in controlled drug delivery in tissue administration, Dissertation, University of Helsinki. pp. i-48. (provided in the Feb. 26, 2009 restriction requirement).*

Kortesuo et al, 2001a. Alkyl-substituted silica gel as a carrier in the controlled release of dexmedetomidine. Journal of Controlled Release, vol. 76:227-238.*

Kosuka et al (Chemistry Materials, vol. 1, No. 4, 1989).*

Wang et al. "Accelerated Sub-critical Drying of Large Alkoxide Silica Gels," 1758 *Sol-Get Optics II*. 113-124 (1992).

Kortesuo et al. "Effect of Synthesis Parameters of the Sol-gel-processed Spray-dried Silica Gel Microparticles on the Release rate of Dexmedetomideine," 23 *Biomaterials*. 2795-2801 (2002).

Venkateswara Rao et al. "Effect of Gel Parameters on Monolithicity and Density of Silica Aerogels," 28 *J. Materials Sci*. 3021-3026 (1993).

Asomoza et al. "Calorimetric Study of the Sol-gel Silica Gelation Stage: Effect of Gelation pH," 33 *Materials Letters*. 153-160 (1997).

Pope et al. "Sol-gel Processing of Silica," 87 *J. Non-Crystalline Solids*. 185-198 (1986).

Ahola et al., "Silica Xerogel Carrier Material for Controlled Release of Toremifene Citrate," 195 *Int'l J. Pharm*. 219 (2000).

\* cited by examiner

METHOD FOR PREPARING ADJUSTABLY BIORESORBABLE SOL-GEL DERIVED SIO$_2$

This application is the U.S. National Stage of International Application No. PCT/FI2005/050046, filed Feb. 22, 2005, which claims benefit of U.S. Provisional Application No. 60/548,113, filed Feb. 27, 2004, and Finnish Application No. 20040312, filed Feb. 27, 2004.

FIELD OF THE INVENTION

The present invention relates to a method for adjusting the bioresorption rate of sol-gel derived SiO$_2$. The present invention further relates to sol-gel derived SiO$_2$ obtainable with the method.

BACKGROUND OF THE INVENTION

The publications and other materials used herein to illuminate the background of the invention, and in particular, cases to provide additional details respecting the practice, are incorporated by reference.

Sol-gel derived SiO$_2$ is commonly prepared from alkoxides or inorganic silicates that via hydrolysis form a sol that contains either partly hydrolysed silica species or fully hydrolysed silicic acid. Consequent condensation reactions of SiOH containing species lead to formation of larger silica species with increasing amount of siloxane bonds. Furthermore, the species aggregate, form nanosized particles and/or larger aggregates until a gel is formed. The sols derived from alkoxides provide possibilities to adjust the siloxane bond formations and aggregation due to possibility for partial hydrolysis. Reactions (typically at ≤40° C.) are commonly catalysed either by mineral acids (such as HCl and HNO$_3$) or bases (such as NH$_3$). The formed gel is then aged (typically at ≤40° C.), dried (typically at ≤40° C.) and/or heat-treated (typically at ≤700° C.) to desired form resulting typically in amorphous and porous SiO$_2$. The last step, heat treatment at elevated temperatures (50-700° C.) is typically skipped if the system contains a biologically active agent. The gels that are dried at moderate temperature (at ≤50° C.) are called xerogels (<Gr. xero=dry). Amorphous and porous sol-gel derived SiO$_2$ is known to be biocompatible and known to dissolve in the living tissue as well as in solutions simulating the inorganic part of real human body fluid, e.g. in a water solution buffered to pH 7.4 at 37° C. with or without inorganic salts found in real body fluids.

The terms used for degradation of a material in or in contact with the living organisms, e.g. living tissue or in contact with plants, microbes etc., are numerous. The terms "biodegradable/biodegradation" are often used as a general definition for degradation in or in contact with living organisms. The terms are also used, especially in connection with carbon-based polymers to describe that the degradation mechanism may include both dissolution in body fluids as well as enzymatic degradation of the polymer matrix. Regarding carbon-based polymers, this often means either decrease in molecular weight or mass loss or both. The terms bioresorbable/bioresorption and bioabsorbable/bioabsorption are often used to describe materials degradation in or in contact with the living organism, mostly for implanted biomaterials in living tissue describing a degradation mechanism mainly governed by dissolution in the body fluids or by a mechanism that is not exactly known. Bioresorption is often used for implantable ceramic biomaterials, such as bioactive glasses or sol-gel derived SiO$_2$. The general terms dissolution/soluble in body fluids are often used for biomaterials implanted into the living tissue. The terms (bio)erosion/(bio)erodable are more often in use in drug delivery, especially as it is desirable to distinguish between the mechanisms that control the release. Surface erosion describes a material that is so hydrophobic that water absorption does not occur and dissolution/degradation occurs on the surface and bulk erodable material allow water absorption.

The importance of bioresorbable materials is growing in controlled release of biologically active agents. It is often desirable to administer drugs as implants or as injected matrices, either in order to achieve local and/or more effective results in a desired tissue or a controlled systemic effect. A large potential group of biologically active agents for this purpose is biotechnologically produced drugs. The number of these drugs is growing fast and it is accelerated by the successful research on the human genome. New biotech drugs are typically larger in size, such as peptides, proteins and polysaccharides, and direct oral administration is difficult due to intestinal decomposition. In addition, bioresorbable matrices are potential materials for optimising the administration of small molecules by implantation, e.g, to avoid administration several times a day or to optimise the patient docility for drug therapy. In addition, bioresorbable materials are potential matrices as it is desirable to avoid extra removal operations that are commonly done for biostable delivery matrices, (such as PDMS, polydimethylsiloxane). Materials having pore sizes between 1-100 nm are in the same order of magnitude as the size of many peptides and proteins, but solely diffusion-controlled release is often far from the optimal.

WO 93/04196 by Zink et al. discloses the idea of encapsulating enzymes in a porous transparent glass, prepared with a sol-gel method. The purpose is to immobilize enzymes in the pore structure and thus, the release of the enzymes is to be avoided. These porous, transparent glasses can be used to prepare sensors for qualitatively and quantitatively detecting both organic and inorganic compounds, which react with the entrapped material. The pore radius in these glasses is so small (under about 4 nm) that the entrapped biologically active materials cannot diffuse out from the glass.

WO96/03117 by Ducheyne et al. discloses controlled release carriers, where biologically active molecules are incorporated within the matrix of a silica-based glass. Here, silica-based glasses are typically multicomponent glasses, and 100% SiO$_2$ is a special case, with a very poor dissolution. The release of the biologically active molecules from the carrier is claimed to occur primarily by diffusion through the pore structure and bioresorption is not mentioned to affect the release of biologically active agents.

WO 97/45367 by Ahola et al. describes controlled dissolvable silica-xerogels prepared via a sol-gel process. The preparation of dissolvable oxides (silica xerogels) is carried out by simultaneous gelation and evaporation and mainly concerns small particles made by spray-drying or fibres made by drawing. WO 01/13924 by Ahola et al. describes controlled release of a biologically active agent from a sol-gel derived silica xerogel. These inventions provide sustained and/or controlled release delivery devices for biologically active agents, but they do not give methods for adjusting bioresorption or merely give very limited means for adjusting bioresorption.

WO 00/50349 by Jokinen et al. and WO 01/40556 by Peltola et al. disclose methods for preparation of sol-gel derived silica fibres. WO 00/50349 discloses a method for adjusting the biodegradation rate of the fibres by controlling the viscosity of the spinning process. WO 01/40556 discloses a method for preparing a bioactive sol-gel derived silica fibre.

WO 02/080977 by Koskinen et al. discloses a method for preparation of a biodegradable silica xerogel comprising infecting and/or transfecting viruses.

The prior art does not provide versatile means for preparing sol-gel derived $SiO_2$ with tailored bioresorption rates. In particular it does not provide means for preparing sol-gel derived $SiO_2$ with a very fast bioresorption rate.

OBJECTS AND SUMMARY OF THE INVENTION

An object of the present invention is to provide a method for preparing a sol-gel derived $SiO_2$ with a very fast bioresorption rate.

Another object of the present invention is to provide a method for adjusting the bioresorption rate of sol-gel derived $SiO_2$.

Still another object of the present invention is to provide a sol-gel derived $SiO_2$ monolith tailored to have a desired bioresorption rate.

A further object of the present invention is to provide a sol-gel derived $SiO_2$ coating tailored to have a desired bioresorption rate.

A still further object of the present invention is to provide a sol-gel derived $SiO_2$ particle tailored to have a desired bioresorption rate.

An object of the present invention is to also provide a method for administering a biologically active agent into a human or animal body, or to a plant.

Thus the present invention provides a method for preparing a sol-gel derived $SiO_2$ monolith, preferably with a minimum diameter of ≥0.5 mm, coating, preferably with a thickness of <0.5 mm, or particle, preferably with a maximum diameter of ≤100 μm, with a very fast bioresorption rate, said $SiO_2$ optionally comprising a specific percentage or percentages of a biologically active agent or agents other than the $SiO_2$ itself with or without protective agent or agents for said biologically active agent or agents, wherein method a sol-gel derived $SiO_2$ is prepared from a sol comprising water, an alkoxide or inorganic silicate and a lower alcohol, i.e. an alcohol with ≤4 carbons, using a mineral acid or a base as a catalyst, preferably a mineral acid, and said sol is aged and dried. Characteristic for the method is that a) in the sol the starting
  i) pH is from 0.05 to 2.5, preferably 1.5 to 2.5, most preferably 2.0,
  ii) molar ratio of water to the alkoxide or inorganic silicate is 0.5 to 2.5; preferably 1.5 to 2.5,
  iii) molar ratio of alcohol to the alkoxide or inorganic silicate is ≥0.5, preferably ≥1.0; and b) either,
  i) the sol is, without induced changes of sol composition, let to gel spontaneously at a temperature of ≤25° C. or an elevated temperature of 65° C. to 90° C., preferably at an elevated temperature of 65° C. to 90° C., or gelation of the sol is done by forced drying of the sol, or
  ii) a change or changes of sol composition are induced after sol ageing but before gel formation, said change or changes of sol composition optionally comprising addition of said biologically active agent or agents with or without said protective agent or agents, and the ratio $t/t_{gel}$ is ≥0.005, preferably ≥0.1, most preferably ≥0.9, wherein
  t is the ageing time of the sol, i.e. time from preparation of said sol to the induced changes, and
  $t_{gel}$ is the time point where the sol would have turned to a gel without the induced changes; and
forced drying of the sol is carried out or initiated within a time of ≤30 minutes, preferably ≤15 minutes, most preferably ≤5 minutes, from said induced change or changes.

The present invention also provides a method for adjusting the bioresorption rate of sol-gel derived $SiO_2$ monolith, preferably with a minimum diameter of ≥0.5 mm, coating, preferably with a thickness of <0.5 mm, or particle, preferably with a maximum diameter of ≤100 μm, optionally comprising a specific percentage or percentages of a biologically active agent or agents other than the $SiO_2$ itself with or without protective agent or agents for said biologically active agent or agents. Characteristic for the method is that a $SiO_2$ with a very fast bioresorption rate is obtained according to the method of preparing a $SiO_2$ as defined above; and a $SiO_2$ with a slower bioresorption rate than the very fast bioresorption rate is obtained by correlating a desired biodegradability of a $SiO_2$ with changes a), b) and/or c) to the method of preparing a $SiO_2$ defined above, wherein a) comprises deviating in the sol any of the starting values:
  i) pH,
  ii) molar ratio of water to the alkoxide or inorganic silicate, and/or
  iii) molar ratio of alcohol to the alkoxide or inorganic silicate;
from the values defined in a) i)-iii) of claim 1;

b) comprises carrying out induced changes by addition of a component or components, including optional addition of the biologically active agent or agents with or without said protective agent or agents, said changes affecting any of the values i)-iii) of a) of claim 1 or a) if applied by
  i) not carrying out forced drying, or
  ii) carrying out or initiating forced drying of the sol later than defined in b) ii) of claim 1; and c) comprises deviating the temperature for letting the sol gel spontaneously from the values defined in b) i) for preparing a $SiO_2$ with a very fast biodegradation rate; and
a method for preparing the $SiO_2$ with changes correlating with the desired biodegradability is carried out for obtaining the $SiO_2$ with the desired slower biodegradability.

The present invention further provides a sol-gel derived $SiO_2$, obtainable according to the method of the invention. Characteristic for the $SiO_2$ is that
a) the $SiO_2$ is a monolith, preferably with a minimum diameter of ≥0.5 mm,
b) the $SiO_2$ comprises no biologically active agent other than the $SiO_2$ itself, and
c) the dissolution rate of the $SiO_2$ in a TRIS buffer at a temperature of +37° C. and pH 7.4 is ≥0.04 wt-%/h, preferably ≥0.07 wt-%/h and more preferably ≥0.15 wt-%/h.

The present invention still further provides a bioresorbable sol-gel derived $SiO_2$, obtainable according to the method of the invention. Characteristic for the $SiO_2$ is that
a) the $SiO_2$ is a monolith, preferably with a minimum diameter of ≥0.5 mm,
b) the $SiO_2$ comprises at least one biologically active agent other than the $SiO_2$ itself, and
c) the dissolution rate of the $SiO_2$ in a TRIS buffer at a temperature of +37° C. and pH 7.4 is ≥0.35 wt-%/h.

The present invention additionally provides a bioresorbable sol-gel derived $SiO_2$, obtainable according to the method of the invention to which it is characteristic that
a) the $SiO_2$ is a coating, preferably with a thickness of <0.5 mm,
b) the $SiO_2$ either comprises no biologically active agent or comprises at least one biologically active agent other than the $SiO_2$ itself, and
c) the dissolution rate of the $SiO_2$ in a TRIS buffer at a temperature of +37° C. and pH 7.4 is ≥0.04 wt-%/h, preferably ≥0.07 wt-%/h and more preferably ≥0.15 wt-%/h.

The present invention moreover provides a bioresorbable sol-gel derived $SiO_2$, obtainable according to the method of the invention to which it is characteristic that
a) the $SiO_2$ is a particle, preferably with a maximum diameter of ≤100 μm,
b) the $SiO_2$ comprises no biologically active agent other than the $SiO_2$ itself, and
c) the dissolution rate of the $SiO_2$ in TRIS buffer at a temperature of +37° C. and pH 7.4 is ≥0.04 wt-%/h, preferably ≥0.07 wt-%/h and more preferably ≥0.15 wt-%/h.

The present invention also provides a bioresorbable sol-gel derived $SiO_2$, obtainable according to the method of the invention to which it is characteristic that
a) the $SiO_2$ is a particle, preferably with a maximum diameter of ≤100 μm,
b) the $SiO_2$ comprises at least one biologically active agent other than the $SiO_2$ itself, and
c) the dissolution rate of the $SiO_2$ in TRIS buffer at a temperature of +37° C. and pH 7.4 is ≥0.5 wt-%/h.

The present invention further provides a bioresorbable sol-gel derived $SiO_2$, obtainable according to the method of the invention to which it is characteristic that
a) the $SiO_2$ is a monolith, preferably with a minimum diameter of ≥0.5 mm,
b) the $SiO_2$ comprises no biologically active agent other than the $SiO_2$ itself, and
c) the dissolution rate of the $SiO_2$ in a TRIS buffer at a temperature of +37° C. and pH 7.4 is from 0.001 to 0.15 wt-%/h, preferably from 0.002 to 0.07 wt-%/h, and from 0.006 to 0.05 wt-%/h.

The present invention further provides a bioresorbable sol-gel derived $SiO_2$, obtainable according to the method of the invention to which it is characteristic that
a) the $SiO_2$ is a monolith, preferably with a minimum diameter of ≥0.5 mm,
b) the $SiO_2$ comprises at least one biologically active agent other than the $SiO_2$ itself, and
c) the dissolution rate of the $SiO_2$ in a TRIS buffer at a temperature of +37° C. and pH 7.4 is from 0.001 to 0.06 wt-%/h, preferably from 0.002 to 0.05 wt-%/h, and from 0.006 to 0.025 wt-%/h.

The present invention still further provides a bioresorbable sol-gel derived $SiO_2$, obtainable according to the method of the invention to which it is characteristic that
a) the $SiO_2$ is a particle, preferably with a maximum diameter of ≤100 μm,
b) the $SiO_2$ comprises no biologically active agent other than the $SiO_2$ itself, and
c) the dissolution rate of the $SiO_2$ in TRIS buffer at a temperature of +37° C. and pH 7.4 is from 0.001 to 0.008, and preferably from 0.002 to 0.003 wt-%/h.

The present invention also provides a bioresorbable sol-gel derived $SiO_2$, obtainable according to the method of the invention to which it is characteristic that
a) the $SiO_2$ is a particle, preferably with a maximum diameter of ≤100 μm,
b) the $SiO_2$ comprises at least one biologically active agent other than the $SiO_2$ itself, and
c) the dissolution rate of the $SiO_2$ in TRIS buffer at a temperature of +37° C. and pH 7.4 is from 0.001 to 0.10 wt-%/h, preferably from 0.002 to 0.07 wt-%/h, and more preferably from 0.006 to 0.05 wt-%/h.

The present invention additionally provides a bioresorbable sol-gel derived $SiO_2$ monolith, preferably with a minimum diameter of ≥0.5 mm, coating, preferably with a thickness of <0.5 mm, or particle, preferably with a maximum diameter of ≤100 μm, obtainable according to the method of the invention to which it is characteristic that said $SiO_2$ comprises a biologically active agent other than the $SiO_2$ itself and said biologically active agent is a peptide, a protein or a cell, wherein the dissolution rate of the $SiO_2$ in TRIS buffer at a temperature of +37° C. and pH 7.4 is ≥0.04 wt-%/h, preferably ≥0.07 wt-%/h and more preferably ≥0.15 wt-%/h.

The present invention further provides a bioresorbable sol-gel derived $SiO_2$ monolith, preferably with a minimum diameter of ≥0.5 mm, coating, preferably with a thickness of <0.5 mm, or particle, preferably with a maximum diameter of ≤100 μm, obtainable according to the method of the invention to which it is characteristic that said $SiO_2$ comprises a biologically active agent other than the $SiO_2$ itself and said biologically active agent is a peptide, a protein or a cell, wherein the dissolution rate of the $SiO_2$ is ≥0.5 wt-%/h and preferably ≥4.0 wt-%/h.

The present invention also provides a bioresorbable sol-gel derived $SiO_2$ monolith, preferably with a minimum diameter of ≥0.5 mm, coating, preferably with a thickness of <0.5 mm, or particle, preferably with a maximum diameter of ≤100 μm, obtainable according to the method of the invention to which it is characteristic that said $SiO_2$ comprises a biologically active agent other than the $SiO_2$ itself and said biologically active agent is a peptide, a protein or a cell, wherein the dissolution rate of the $SiO_2$ in TRIS buffer at a temperature of +37° C. and pH 7.4 is from 0.001 to 0.15 wt-%/h, preferably from 0.002 to 0.07 wt-%/h, and more preferably from 0.006 to 0.05 wt-%/h.

The present invention also provides a method of use of a bioresorbable sol-gel derived $SiO_2$ monolith, coating or particle according to the invention as defined above for administering a biologically active agent to a human or animal body, wherein said use comprises administering selected from the group consisting of oral, buccal, rectal, parenteral, pulmonary, nasal, ocular, intrauterine, vaginal, urethral, topical, transdermal and surgically implantable administering.

The present invention additionally provides a method of use of a bioresorbable sol-gel derived $SiO_2$ monolith, coating or particle according to the invention as defined above for administering a biologically active agent to a plant.

DETAILED DESCRIPTION OF THE PREFERRED EMBODIMENTS

Terms

Figure 1:
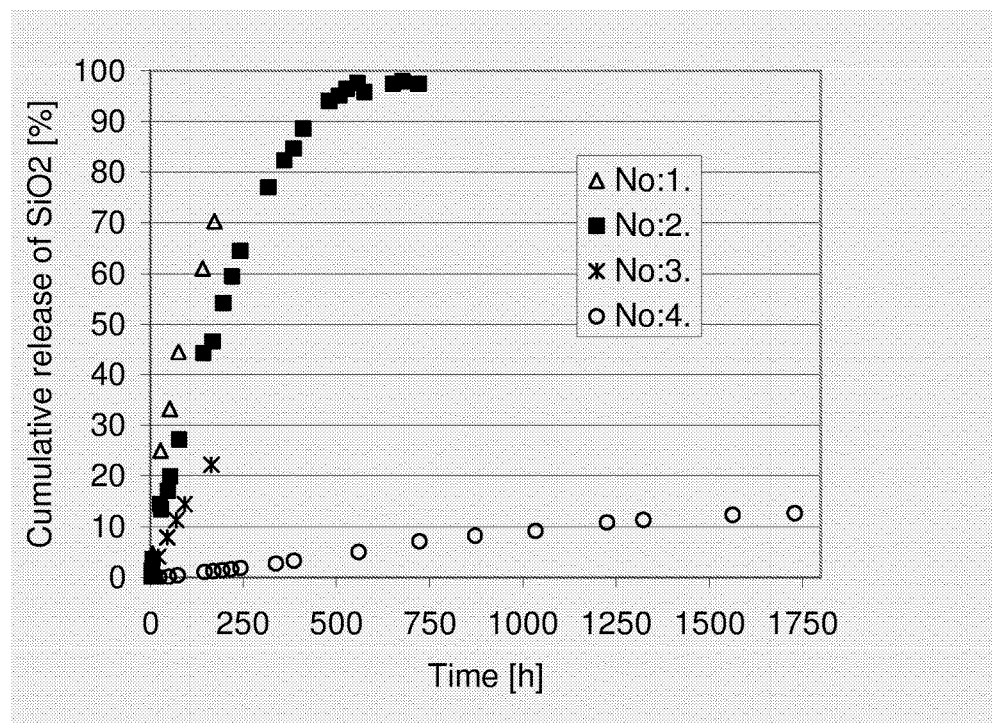
FIG. 1 shows dissolution of $SiO_2$ monolith matrices according to the invention.

The term sol-gel derived $SiO_2$ refers to a $SiO_2$ prepared by the sol-gel process wherein the $SiO_2$ is prepared from a sol comprising $SiO_2$ that has turned to a gel. Sol-gel derived $SiO_2$ is typically prepared from alkoxides or inorganic silicates that via hydrolysis form a sol that contains either partly hydrolysed silica species or fully hydrolysed silicic acid. Consequent condensation reactions of SiOH containing species lead to formation of larger silica species with increasing amount of siloxane bonds. Furthermore, the species aggregate, form nanosized particles and/or larger aggregates until a gel is formed. In the form of a gel, the solid state dominates, but the system still contains varying amounts of liquids and the material is typically soft and viscoelastic before drying and hard and brittle if it is extensively dried. In the form of a sol, liquid state dominates, but the system contains varying amounts of solid phase(s) and the system is still flowing.

Ageing of the sol shall be understood to mean that after initial preparation of the sol the sol is let to be (i.e. reactions and/or aggregations go on without induced changes in composition) without spontaneous drying or with simultaneous, spontaneous drying in ambient conditions until changes are induced or, if no changes are induced, until it turns to a gel spontaneously. The time from preparation until changes are induced, or if no changes are induced until the sol turns to a gel is referred to as sol ageing time. Spontaneous drying typically occurs when the sol is aged so that the system allows evaporation in ambient conditions. Optionally, this is prevented by keeping the sol in a closed system.

In the context of this application the phrase in the sol the starting pH/molar ratio refers to pH/molar ratio at the time when the sol is prepared, i.e. when the original components of the sol are mixed (excluding those components that are optionally added after ageing of the sol).

In the context of this application the phrase induced change or changes of sol composition shall be understood to mean any change intentionally induced to the composition of the sol. It can be a change of composition induced by adding more of one or more of the original components of the sol, e.g. water, the alkoxide or inorganic silicate, the alcohol or the catalyst, i.e. a mineral acid or a base. It can be a change of composition by adding one or more new components to the sol, e.g. a biologically active agent if it changes e.g. the pH of the sol, an acid, base or buffer to adjust the pH, or any other component needed to obtain a desired property of the final $SiO_2$. It can be a sudden physical change affecting the composition of the sol. Such a physical change can for example be elevation of the temperature or decrease in pressure resulting in a sudden release of volatile components (e.g. water, alcohol, and/or volatile acid or base) of the sol, e.g. sudden forced drying, such as spray drying. Such a physical change could also be subjecting the sol to different forms of energy, e.g. electromagnetic or acoustic energy, which could result in a pronounced change in the composition.

Component or components to be added to induce changes refer to any component added irrespective of whether the component or components are original constituents of the sol or a biologically active agent or agents, or an agent or agents protecting the biologically active agent or agents.

Gel formation shall be understood to mean the time point when the sol turns to a gel, as the solid phase becomes dominant, i.e. the continuous phase, in contrary to that of the sol where the liquid phase dominates. In the form of a gel, the solid state dominates, but the system still contains varying amounts of liquids and the material is typically soft and viscoelastic before drying, and hard and brittle if it is extensively dried. In the form of a sol, the liquid state dominates, but the system contains varying amounts of solid phase(s) and the system is still flowing.

Ageing of the gel should be understood to mean that after gel formation the gel is let to be, either without spontaneous drying or with simultaneous, spontaneous drying.

Biologically active agent in the context of this application refers to any organic or inorganic agent that is biologically active, i.e. it induces a statistically significant biological response in a living tissue, organ or organism. The biologically active agent can be a medicine, peptide, protein, polysaccharide or a polynucleotide. It can be a living or dead cell or tissue, bacteria, a virus, a bacteriophage and a plasmid or a part thereof. It can be an agent for treatment of diseases in therapeutic areas like alimentary/metabolic, blood and clotting, cardiovascular, dermatological, genitourinary, hormonal, immunological, infection, cancer, musculoskeletal, neurological, parasitic, ophthalmic, respiratory and sensory. It can further be for treatment of diseases like osteoporosis, epilepsy, Parkinson's disease, pain and cognitive dysfunction. It can be an agent for the treatment of hormonal dysfunction diseases or hormononal treatment e.g for contraception, hormonal replacement therapy or treatment with steroidal hormones. It can further be an agent such as an antibiotic or antiviral, anti-inflammatory, neuroprotective, prophylactic vaccine, memory enhancer, analgesic (or analgesic combination), immunosuppressant, antidiabetic or an antiviral. It can be an antiasthmatic, anticonvolsant, antidepressant, antidiabetic, or antineoplastic. It can be an antipsychotic, antispasmodic, anticholinergic, sympatomimetic, antiarrytthimic, antihypertensive, or diuretics. It can be an agent for pain relief or sedation. It can also be a tranquilliser or a drug for cognitive dysfunction. The agent can be in a free acid or base form, a salt or a neutral compound. It can be a peptide, e.g. levodopa; a protein, e.g. a growth factor; or an antibody. It can be a polynucleotide, a soluble ion or a salt.

Protecting agent or agents in the context of this application refer to a substance or substances that are useful for protecting and/or enhancing the biological activity of a biologically active agent.

In the context of this application the term forced drying refers to the use of a drying process comprising a sudden physical change that stops or highly slows down the reactions in the sol leading to the formation of the gel. The physical change can be a change that speeds up the rate of drying; preferably at least momentarily more than ten fold. Such a physical change can for example be pronounced elevation of the temperature and/or decrease in pressure resulting in a sudden release of volatile components (e.g. water, alcohol, and/or volatile acid or base) of the sol. Such a physical change could also be subjecting the sol to different forms of energy, e.g. electromagnetic or acoustic energy. The physical change can also be an essential decrease of the temperature, preferably freezing the sol, so as to stop or essentially slow down the reactions leading to gel formation. Typically forced drying of the sol is by spray-drying or freeze-drying. Initiation of forced drying refers to, e.g. in the case of freeze-drying to freezing of the sol.

The term dissolution rate refers to $SiO_2$ matrix resorption in TRIS (e.g., Trizma pre-set Crystals, Sigma) solution buffered at pH 7.4 and 37° C. that simulates conditions of body fluids. The TRIS solution is from 0.005 M to 0.05 M. In practice the concentration of TRIS solution is varied according to specific demands of the analysis of a biologically active agent since determination of the release rate of the biologically active agent is typically carried out when the dissolution rate of the matrix is determined. It is common that buffers interfere with many analysis systems that include specific reagents that interact with the analysed target molecule. Such interference is often connected to certain buffer concentration.

Determination of the dissolution rate is carried out as follows: The TRIS buffer is sterilized at 122° C. before use. The $SiO_2$ concentration in the TRIS is kept below 30 ppm (to ensure in sink conditions; free dissolution of the $SiO_2$ matrix) during dissolution. The $SiO_2$ saturation level at pH 7.4 is about 150 ppm. When needed, a portion of the dissolution medium is changed to a fresh TRIS buffer in order to keep the $SiO_2$ concentration below 30 ppm. The dissolution rate is measured from the linear phase of the release curve that is typical after a typical initial deviation (slower or faster phase of release than the linear main part of the release) and before a typical slower phase of the release before the total 100% $SiO_2$ dissolution. The linear phase of the release is typically longer than the deviating phases in the beginning or in the end release. The linear phase of the release curve (wt-% dissolved $SiO_2$/h) can be defined by making a linear regression analysis of the measured release points (wt-% dissolved $SiO_2$/h). Points of a possible initial deviation phase (slower or faster phase of release than the linear main part of the release) are excluded if the points decrease the linear regression correlation factor ($r^2$) to be <0.9. The linear phase of the release curve (wt-% dissolved $SiO_2$/h) can be defined by making a linear regression analysis of measured release points (wt-% dissolved $SiO_2$/h) with a linear regression correlation factor ≥0.9. The total amount (100 wt-%) of $SiO_2$ is calculated from the theoretical amount of $SiO_2$ that can be obtained from the sol composition according to the net reaction (e.g. 1 mol of used alkoxide, TEOS corresponds to 1 mol $SiO_2$).

The term cell means any living or dead cell of any organism. Thus cells of e.g. any animal, such as a mammal including a human, plant, bacteria and fungi are included.

The term coating refers to in the context of this application any coat on any surface. It especially means a coat with a thickness of <0.5 mm.

Features of the Invention

The present invention relates generally to biocompatible and bioresorbable sol-gel derived $SiO_2$ useful e.g. for drug delivery matrices, in tissue engineering, regenerative medicine and cell therapy in the living tissue or in contact with other living organisms, e.g. plants. The use of sol-gel derived $SiO_2$ can e.g. be oral, buccal, rectal, parenteral (e.g. subcutaneous administration, intramuscular administration, intravenous administration and intra-arterial administration), pulmonary, nasal, ocular, intrauterine, vaginal, urethral, topical, transdermal and surgically implantable delivery of monoliths, coatings, or nano- or microparticles as such or in suspension. The bioresorption of the $SiO_2$ matrices can be controlled by simple adjustments of the precursor ratios that influence condensation and aggregation of hydrolysed silica species. The bioresorbable matrices obtainable by this invention can be applied for releasing different types of biologically active agents in a controlled manner dependent on the $SiO_2$ matrix bioresorption.

The present invention provides methods to control the bioresorption of sol-gel derived $SiO_2$. The control of bioresorption is based mainly on the precursor ratio adjustments and specific process parameters that quench the reactions affecting the bioresorption. The adjustably bioresorbable matrices can be utilised in the controlled release of biologically active agents. The biologically active agent can be e.g. in the form of salt like selegiline hydrochloride or in the form of free acid (ibuprofen) or free base (miconatzole) or a neutral compound. The biologically active agent can be a peptide, e.g. levodopa, a protein also an enamel matrix derivative of a protein or a bone morphogenetic protein. An effective amount of a biologically active agent can be added to the reaction at any stage of the process. The dissolving $SiO_2$ matrix may also itself act as a biologically active agent, especially in bone, where the dissolved silica species are known the affect the formation of new bone. The adjustably bioresorbable sol-gel derived $SiO_2$ can also be used in contact with other living organisms, e.g., in contact of cell walls of plants to enhance plants' performance, e.g. against diseases. The biologically active agent can further be an agent with a biological effect on any tissue, cell or organism as defined and exemplified earlier.

Sol-gel derived $SiO_2$ is a very suitable material to be used for controlled release. Its contact with a living tissue is good, i.e., it is non-toxic and biocompatible. The nature of the sol-gel process that starts from a sol in the liquid phase makes it easy to add biologically active agents and if desired, the temperature can be kept at ≤40° C. during the whole process and the pH can largely be adjusted. In addition, amorphous $SiO_2$ is bioresorbable at pH 7.4 and 37° C. Amorphous $SiO_2$ can be prepared by several ways, e.g., by a conventional high temperature melting-cooling process to produce glasses, but the use of the sol-gel process in the preparation of amorphous $SiO_2$ provides the best possibilities to adjust bioresorption as well as preserve the biological activity of the encapsulated agent. Bioresorption depends both on chemical structure (e.g., the number of free SiOH groups or degree of condensation) of the $SiO_2$ as well as on the pore structure. The denser the gel structure is the more important is the size of the material with respect to the bioresorption. If, e.g. a $SiO_2$ monolith or a particle has a very large surface area, such as several hundreds $m^2/g$, it usually contains also a lot of nanosized pores, which means that grinding of the monoliths or particles to be smaller, e.g. from 1 cm to 50 µm, does not significantly increase the surface area, only the diffusion path length becomes shorter. In the case of a dense $SiO_2$ monolith or a particle, both surface area and diffusion path length are strongly affected by grinding. Chemical and pore structure can be adjusted on a large scale by the sol-gel process. In addition to adjusting the precursor concentrations, the pore structure is commonly adjusted using additional organic templates (e.g., mesoporous MCM-41-type $SiO_2$), but most of the organic templates are not biocompatible and the pore structure can be adjusted well enough (with respect to the bioresorption) without any organic additives.

The mechanism of the release of a biologically active agent from the prepared $SiO_2$ may be diffusion or resorption controlled or a combination of both, but in any case, the role of bioresorption in the overall release rate of biologically active agents can be adjusted to be significant.

The present invention provides methods to prepare and adjust the bioresorption rates of $SiO_2$ on a large scale. This can be done by a alkoxy-based sol-gel or inorganic silicate method at conditions that can be adjusted to be friendly for several kinds of biologically active agents by adjusting the precursor ratios (water-to-alkoxide ratio, alcohol amount, pH), ageing of the sol and by using different preparation methods [e.g. ageing and gel formation and drying of the sol or the gel in a heat oven in normal atmosphere or in the 100% or partial gas (e.g. $N_2$) atmosphere, or drying of the sol or gel by vacuum, electromagnetic energy, acoustic energy, spray-drying or freeze-drying]. The morphologies that can be prepared include monoliths (e.g, sticks, rods, tablets etc.), coatings, nano- and microspheres mainly for oral, buccal, rectal, parenteral, pulmonary, nasal, ocular, intrauterine, vaginal, urethral, topical, transdermal and surgically implantable administration or for tissue engineering, regenerative medicine and cell therapy. In addition, the amount of biologically active agent in the $SiO_2$ matrix, the biologically active agent itself, ageing and drying temperature and the drying process conditions affect the bioresorption, but the main factor that controls the overall bioresorption rate is the ratio of precursors. It should also be noted that large amounts of the biologically active agent, protective agent for said biologically active agent or any additional substance of the sol comprised within the $SiO_2$ matrix increases dissolution of $SiO_2$, simply due to their presence making the $SiO_2$ structure more hetergenous.

The invention provides a specific narrow range of precursor ratios that result in fast dissolving $SiO_2$ structure and all deviations from this make the $SiO_2$ matrix dissolve slower in aqueous solutions at a pH from 7.0 to 7.5. In addition, the invention provides means to deviate from the chosen precursor ratios for a short time without loosing the original effect of the original precursor ratios on the $SiO_2$ bioresorption.

$SiO_2$ matrices dissolving very fast can be prepared, e.g. from alkoxides at conditions where the rate of hydrolysis is relatively fast, but the rate of condensation is at minimum, near a molar water to alkoxide (e.g. TEOS) ratio (R-value) of about 2 at a pH of about 2 and a high enough molar ratio of alcohol (e.g. EtOH) to alkoxide (e.g., TEOS) of about 1. These sols are formed, further aged and optionally also dried at low temperatures, preferably at ≤50° C., (low enough to preserve biological activity of an optionally comprised biologically active agent or agents) until a gel is formed. The gels can also aged and/or dried at low temperatures, preferably at ≤50° C. Alternatively, if no termolabile biologically active agent is comprised high or even very high temperatures, up to e.g. 700° C., can be used.

Some methods of sol drying allow also short-time deviations from the chosen precursor ratio without loosing the original effect of the original precursor ratio on the $SiO_2$ bioresorption. These methods lead to forced gel formation and practically stop or highly slow down, preferably quench all (e.g. condensation) reactions that affect the bioresorption rate (decreasing amount of SiOH during the condensation decreases the $SiO_2$ dissolution rate). The ageing time for the sol can be freely chosen before the short-time affecting adjustments. Short time affecting adjustments can for example be an adjustment of pH to a pH from 5 to 7 and/or addition of water to decrease the relative amount of ethanol if required in order to maintain the biological activity of the ingredient. The ageing time affects the relative ratios of reacted silica species. After the desired ageing time of the sol, it is either spray or freeze dried so that the effect of deviations is short, preferably ≤5 minutes, but at least faster than ≤30 minutes. For microparticles made by spray-drying, deviation from the optimal fast-dissolving precursor ratio by diluting the sol with $H_2O$ and/or alcohol, e.g. EtOH, makes it possible to prepare fast-dissolving microparticles. Spray-drying of the undiluted sol at high $t/t_{gel}$-values (≥0.9) is sometimes impossible due to its high viscosity.

$SiO_2$ monoliths, coatings and particles of the invention can be produced in a variety of ways already known in prior art. Thus monoliths can be produced by casting aliquots of the sol-gel in moulds and letting the sol-gel gel in the mould. Coatings can be produces by applying sol-gel on surfaces and letting the sol-gel gel on the surface. Particles can be produced directly e.g. by spray drying but also indirectly e.g. by crushing monoliths.

It should be noted that due to the versatile possibilities for adjusting the bioresorption rate of the $SiO_2$ provided by the method of the invention it is possible to obtain $SiO_2$ monoliths, coatings and particles with bioresorption rates that have not been achieved by the methods of prior art. Until now $SiO_2$ monoliths, coatings and particles have not been very attractive alternatives for many applications due to difficulties in obtaining $SiO_2$ monoliths, coatings and particles with desired properties. In many applications it is of utmost importance that e.g. the bioresorption rate of the $SiO_2$ monoliths, coatings or particles is what has specifically been desired and the bioactive agents incorporated have remained intact when preparing the $SiO_2$. The method of the present invention provides several means for adjusting the bioresorption rate within the method and thus it is most often possible to choose the particular means so that bioactive agents sensitive to changes, especially changes of prolonged duration, in e.g. pH and/or temperature are not harmfully affected by method used to produce the $SiO_2$.

The present invention provides a highly feasible method for producing sol-gel derived $SiO_2$ monolith, coating or particle with any dissolution rate. Thus, $SiO_2$ monoliths, coatings or particles with dissolution rates not achieved with prior art methods as well as those that have been or could have been achieved with prior art methods can be easily produced with the method of the invention.

It should also be noted that the present invention makes it feasible to use sol-gel derived $SiO_2$ obtainable according to the method of the invention for administering a biologically active agent to a human or animal body wherein said use comprises administering selected from the group consisting of oral, buccal, rectal, parenteral, pulmonary, nasal, ocular, intrauterine, vaginal, urethral, topical and transdermal administering. The invention makes it also feasible to use sol-gel derived $SiO_2$ obtainable according to the method of the invention for administering a biologically active agent to a plant.

Preferred Embodiments

Typically an alkoxide, preferably tetraethoxysilane (TEOS), is used for preparing the sol-gel derived $SiO_2$. If an inorganic silicate is used for preparing the sol-gel derived $SiO_2$ it is preferably sodium or potassium silicate. The lower alcohol is preferably ethanol.

The sol, without induced changes of sol composition, can be let to gel spontaneously at a temperature of ≤25° C. or an elevated temperature of 65° C. to 90° C. At a temperature of ≤25° C. the heterogenic structure of the gel might result in fast bioresorption. At a preferred elevated temperature of 65° C. to 90° C. the gellificatiton reaction is fast resulting in a gel with a fast bioresorption rate.

If an induced change or changes of the composition of the sol is carried out, the change or changes are preferably selected from the group consisting of adding water, adding the alkoxide or inorganic silicate, adding the alcohol, adjusting pH by adding an acid or base, preferably the acid or base used as the catalyst, adding the optional bioactive agent or agents with or without protective agent or agents for said biologically active agent or agents affecting pH, molar ratio of water to the alkoxide or inorganic silicate, and/or molar ratio of alcohol to the alkoxide or inorganic silicate, and any combination thereof.

Drying of the sol can be drying by ambient heat, vacuum drying, electromagnetic drying, acoustic drying, spray-drying or freeze-drying, preferably spray-drying or freeze-drying. Forced drying of the sol can be carried out by spray-drying or freeze-drying. Freeze-drying can be initiated by freezing the sol.

The temperature of the sol is typically ≤+90° C., preferably ≤+50° C., most preferably ≤+40° C.

The gel obtained can be dried. Drying of the gel is typically drying by ambient heat, vacuum drying, electromagnetic drying, acoustic drying, spray-drying or freeze-drying, preferably ambient heat or freeze-drying. The gel is typically dried at a temperature of ≤700° C., preferably ≤50° C., and most preferably ≤40° C.

A value that can be deviated to obtain a slower bioresorption rate is the ratio of water to the alkoxide or inorganic silicate, and the more the ratio of water to alkoxide or inorganic silicate is deviated to be higher or lower the slower the bioresorption rate obtained. Another value that can be deviated to obtain a slower bioresorption rate is the ratio of alcohol to the alkoxide or inorganic silicate, and the more the ratio is deviated to be higher or lower the slower the bioresorption rate obtained. The ratio of alcohol to alkoxide can be deviated to be as low as zero, i.e. the sol would originally comprise no alcohol. A further parameter that can be deviated to obtain a slower bioresorption rate is the pH, and the more the pH is deviated to be higher or lower the slower the bioresorption rate obtained.

A great change in molar ratio of water to alkoxide, e.g. from 2 to 50 or even up to 100, by adding water would simultaneously make the sol more biocompatible, e.g. the alcohol concentration would become lower.

A biologically active agent or agents can be added to the sol before gel formation. The biologically active agent or agents can be any agent inducing a biological response in a living tissue, organ or organism as defined and exemplified above. Typical biologically active agents are selected from the group consisting of a drug, peptide, protein, hormone, growth factor, enzyme, polysaccharide, living or dead cells or viruses or parts thereof, plasmids, polynucleotides, water soluble ions, salts and any combination thereof.

The pH value, molar ratio value of water to the alkoxide or inorganic silicate, and/or molar ratio value of alcohol to the alkoxide or inorganic silicate can be changed to deviate from the ranges with which a very fast bioresorption rate is obtained, after sol ageing but before gel formation and/or optional addition of said biologically active agent or agents if within ≤30 minutes, preferably ≤15 minutes and most preferably ≤5 minutes, from the change forced drying of the sol is carried out or initiated.

The sol-gel derived $SiO_2$ is a monolith, preferably with a minimum diameter of ≥0.5 mm; a coating, preferably with a thickness of <0.5 mm; or a particle, preferably with a maximum diameter of ≤100 μm.

Preferred dissolution rates of $SiO_2$ depend on which applications the $SiO_2$ is intended for. For many applications, such as oral, buccal, rectal, pulmonary, transdermal and other parenteral applications, high dissolution rates are required.

Monoliths, preferably with a minimum diameter of 0.5 mm, without a biologically active agent other than the $SiO_2$ itself typically have a dissolution rate of the $SiO_2$ in TRIS buffer at a temperature of +37° C. and pH 7.4 that is ≥0.04 wt-%/h, preferably ≥0.07 wt-%/h and more preferably ≥0.15 wt-%/h.

Coatings, preferably with a thickness of <0.5 mm, comprising no biologically active agent other than the $SiO_2$ itself or comprising at least one biologically active agent other than the $SiO_2$ itself typically have a dissolution rate of the $SiO_2$ in IRIS buffer at a temperature of +37° C. and pH 7.4 that is ≥0.04 wt-%/h, preferably ≥0.07 wt-%/h and more preferably ≥0.15 wt-%/h.

Particles, preferably with a maximum diameter of ≤100 μm, comprising no biologically active agent other than the $SiO_2$ itself typically have a dissolution rate of the $SiO_2$ in TRIS buffer at a temperature of +37° C. and pH 7.4 that is ≥0.04 wt-%/h, preferably ≥0.07 wt-%/h and more preferably ≥0.15 wt-%/h. A particle, preferably with a maximum diameter of ≤100 μm, comprising at least one biologically active agent other than the $SiO_2$ itself typically have a dissolution rate of the $SiO_2$ in TRIS buffer at a temperature of +37° C. and pH 7.4 that is ≥0.5 wt-%/h.

For some purposes high, very high and extremely high dissolution rates are preferable. Especially preferred dissolution rates of the $SiO_2$ for the monoliths, coatings and/or particles can for these purposes be up to ≥0.30 wt-%/h, ≥0.5 wt-%/h, ≥1.0 wt-%/h, ≥2.0 wt-%/h, a ≥4.0 wt-%/h, ≥6.0 wt-%/h, ≥8.0 wt-%/h and even ≥10.0 wt-%/h depending on the particular application. The fastest dissolution rates are preferable for e.g. oral preparations.

In other cases long term dissolution rates are required for instance for certain parenteral applications, tissue engineering and regenerating medicine applications.

A monolith, preferably with a minimum diameter of ≥0.5 mm, comprising no biologically active agent other than the $SiO_2$ itself can typically have a dissolution rate of the $SiO_2$ in a TRIS buffer at a temperature of +37° C. and pH 7.4 that is from 0.001 to 0.15 wt-%/h, preferably from 0.002 to 0.07 wt-%/h, and more preferably from 0.006 to 0.05 wt-%/h.

A monolith, preferably with a minimum diameter of ≥0.5 mm, comprising at least one biologically active agent other than the $SiO_2$ itself can typically have a dissolution rate of the $SiO_2$ in a TRIS buffer at a temperature of +37° C. and pH 7.4 that is from 0.001 to 0.06 wt-%/h, preferably from 0.002 to 0.05 wt %/h, and more preferably from 0.006 to 0.025 wt-%/h.

A coating, preferably with a thickness of <0.5 mm, comprising no biologically active agent other than the $SiO_2$ itself or comprising at least one biologically active agent other than the $SiO_2$ itself can typically have a dissolution rate of the $SiO_2$ in TRIS buffer at a temperature of +37° C. and pH 7.4 that is from 0.001 to 0.15 wt-%/h, preferably from 0.002 to 0.07 wt-%/h, and more preferably from 0.006 to 0.05 wt-%/h.

A particle, preferably with a maximum diameter of ≤100 μm, comprising no biologically active agent other than the $SiO_2$ itself can typically have a dissolution rate of the $SiO_2$ in TRIS buffer at a temperature of +37° C. and pH 7.4 that is from 0.001 to 0.008, and preferably from 0.002 to 0.003 wt-%/h.

A particle, preferably with a maximum diameter of ≤100 µm, comprising at least one biologically active agent other than the $SiO_2$ itself can typically have a dissolution rate of the $SiO_2$ in TRIS buffer at a temperature of +37° C. and pH 7.4 that is from 0.001 to 0.10 wt-%/h, preferably from 0.002 to 0.07 wt-%/h, and more preferably from 0.006 to 0.05 wt-%/h.

A bioresorbable sol-gel derived $SiO_2$, obtainable according to the method of the invention comprising a biologically active agent other than the $SiO_2$ itself that is a peptide, protein or cell typically has a dissolution rate of the $SiO_2$ in TRIS buffer at a temperature of +37° C. and pH 7.4 that is ≥0.04 wt-%/h, preferably ≥0.07 wt-%/h and more preferably ≥0.15 wt-%/h. For some applications an even more preferable dissolution rate is ≥0.5 wt-%/h and even ≥4.0 wt-%/h. Fore other applications a typical dissolution rate can be from 0.001 to 0.15 wt-%/h, preferably from 0.002 to 0.07 wt-%/h, and more preferably from 0.006 to 0.05 wt-%/h.

EXAMPLES

Example 1

Matrix dissolution was studied by immersing silica monoliths in 0.005or 0.05 M TRIS buffer solution (pH 7.4, 37° C.) in in sink conditions ($SiO_2$<30 ppm). The TRIS buffer was sterilized at 121° C. before use. The dissolution studies were done in the shaking water bath. The Si concentration of the TRIS buffer at different time points was measured with a spectrophotometer (UV-1601, Shimadzu) analysing the molybdenum blue complex absorbance at 820 nm. The dissolution of the matrix is presented as cumulative release of $SiO_2$ from the matrix. The total amount (100%) of $SiO_2$ is calculated from the theoretical amount of $SiO_2$ that can be obtained from the sol composition according to the net reaction (1 mol of used alkoxide, TEOS corresponds to 1 mol $SiO_2$).

The dissolution of $SiO_2$ monolith matrices 1 to 4 of example 1 are presented in FIG. 1.

Matrix 1 (FIG. 1)

The initial sol concentration (mol ratio) and calculated pH were: $H_2O$/TEOS=2, ethanol/TEOS=1, pH 2 (HCl was used to adjust the pH). Hydrolysis of the sol was done at room temperature. The sol was aged and dried simultaneously at 40° C. for 65 hours. After ageing and drying the pH of the sol was raised with 0.5 M NaOH to 6.3. 200 ml of the sol was pipetted into the test-tube and sank into liquid nitrogen in order to freeze the samples. After that the samples were freeze dried in vacuum. The calculated $SiO_2$ dissolution rate was 0.407 wt-%/h.

Matrix 2 (FIG. 1)

The initial $H_2O$/TEOS (mol ratio) and calculated pH were: $H_2O$/TEOS=30, pH 2.8 (HCl was used to adjust the pH). Hydrolysis was done at room temperature. The pH of the sol was raised with 1 M $NH_3$ to 5.1. The sol was then pipetted into the mould and aged for 1 hour in a closed system and after that the gel was aged and dried simultaneously at 40° C. Drying of the gel occurred at 40° C. with free evaporation to constant weight. The calculated $SiO_2$ dissolution rate was 0.179 wt-%/h.

Matrix 3 (FIG. 1)

The initial concentration (mol ratio) and calculated pH were: $H_2O$/TEOS=15, pH 2 (HCl was used to adjust the pH). Hydrolysis of the sol was done at room temperature. The sol was aged and dried at 40° C. for 42 hours. After that the sol was pipetted into the mould and aged for 29 h at 4° C. in the closed mold. Drying and ageing of the sol and gel occurred at 4° C. with free evaporation to constant weight. The calculated $SiO_2$ dissolution rate was 0.131 wt-%/h.

Matrix 4 (FIG. 1)

The initial sol concentration (mol ratio) and calculated pH were: $H_2O$/TEOS=3, pH 2 (HCl was used to adjust the pH). Hydrolysis was done at room temperature. The sol was pipetted in to the mould and aged at 40° C. for 145.5 h. Drying of the gel occurred at 40° C. with free evaporation to constant weigh. The calculated $SiO_2$ dissolution rate was 0.008 wt-%/h.

Example 2

Matrix dissolution was studied by immersing silica microspheres in 0.005 or 0.05 M TRIS buffer solution (pH 7.4, 37° C.) in in sink conditions ($SiO_2$<30 ppm). TRIS was sterilized at 121° C. before use. The dissolution studies were done in the shaking water bath. The Si concentration of the TRIS at different time points was measured with spectrophotometer (UV-1601, Shimadzu) analysing the molybdenum blue complex absorbance at 820 nm. The dissolution of the matrix is presented as cumulative release of $SiO_2$ from the matrix. The total amount (100%) of $SiO_2$ is calculated from the theoretical amount of $SiO_2$ that can be obtained from the sol composition according to the net reaction (1 mol of used alkoxide, TEOS corresponds to 1 mol $SiO_2$).

Figure 2:
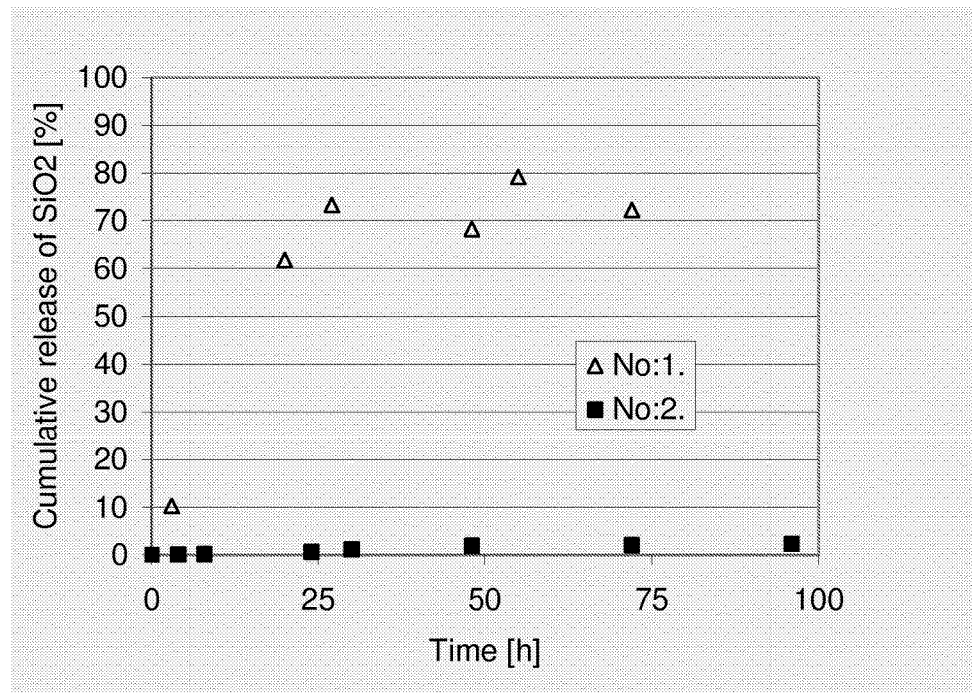
FIG. 2 shows dissolution of $SiO_2$ microspheres according to the invention.

The dissolution of $SiO_2$ monolith microspheres 1 and 2 of example 2 are presented in FIG. 2.

Microsphere 1 (FIG. 2)

The initial concentration (mol ratio) and calculated pH were: $H_2O$/TEOS=2, pH 2, ethanol/TEOS=1 (HCl was used to adjust the pH). Hydrolysis was done at room temperature. The sol was aged and dried simultaneously at 40° C. for 22 hours. After that water and ethanol was added into the sol changing the $H_2O$/TEOS mol ratio to 15 and ethanol/TEOS to 5.3. After that pH of the sol was adjusted with 5 M NaOH to 6.9. Microspheres were prepared by spraying silica sol with a mini spray dryer (B-191, Büchi Labortechnik AG, Switzerland) within 15 minutes after water and ethanol addition and pH adjustment to 6.9. The following process parameters were used: pump 16%, aspirator 95%, and flow 600 l/h. The temperature of the spray nozzle was 120° C. The calculated $SiO_2$ dissolution rate was 2.70 wt-%/h.

Microsphere 2 (FIG. 2)

The initial concentration (mol ratio) and calculated pH were: $H_2O$/TEOS=30, pH 2.8 (HCl was used to adjust the pH). Hydrolysis was done at room temperature. The pH of the sol was adjusted after the sol hydrolysis with 1 M $NH_3$ to 5. Microspheres were prepared by spraying silica sol with a mini spray dryer (B-191, Büchi Labortechnik AG, Switzerland) within 15 minutes after the pH adjustment to 5. The following process parameters were used: pump 16%, aspirator 95%, and flow 600 l/h. The temperature of the spray nozzle was 135° C. The calculated $SiO_2$ dissolution rate was 0.026 wt-%/h.

Example 3

$SiO_2$ monoliths were prepared in the following way, the initial concentration (mol ratio) and calculated pH were: $H_2O$/TEOS=3, pH 2 (HCl was used to adjust the pH). Hydrolysis was done at room temperature. Propranolol (drug) was added into the sol. The amount of propranolol was 5 weight-% of the theoretical $SiO_2$ amount in the sol (1 mol TEOS=1 mol $SiO_2$). After the propranolol had dissolved the sol was pipetted into the mould and aged at 40° C. for 145.5 h. Drying of the gel occurred at 40° C. with free evaporation to the constant weight.

Matrix dissolution and propranolol release was studied by immersing silica monoliths in 0.005 M TRIS buffer solution (pH 7.4, 37° C.) in in sink conditions ($SiO_2$<30 ppm) and 0.005 M TRIS buffer solution (pH 7.4, 37° C.) saturated with $SiO_2$ ($SiO_2$ 120-130 ppm). TRIS was sterilized at 121° C. before use. The dissolution studies were done in a shaking water bath. In a $SiO_2$ saturated TRIS solution the $SiO_2$ concentration does not increase even if a dissoluble silica matrix is placed into the solution. The Si concentration of the TRIS buffer at different time points was measured with a spectrophotometer (UV-1601, Shimadzu) analysing the molybdenum blue complex absorbance at 820 nm. The dissolution of the matrix in TRIS is presented as cumulative release of $SiO_2$ matrix. The total amount (100%) of $SiO_2$ is calculated from the theoretical amount of $SiO_2$ that can be obtained from the sol composition according to the net reaction (1 mol of used alkoxide, TEOS corresponds to 1 mol $SiO_2$). No matrix dissolution was observed in $SiO_2$ saturated TRIS. In a $SiO_2$ saturated TRIS solution the $SiO_2$ concentration does not increase even if a dissolving silica matrix is placed into the solution. The propanolol concentration is measured directly with spectrophotometer at a wavelength of 227 nm. The release of the propranolol in TRIS and in $SiO_2$ saturated TRIS is presented as cumulative release.

Figure 3:
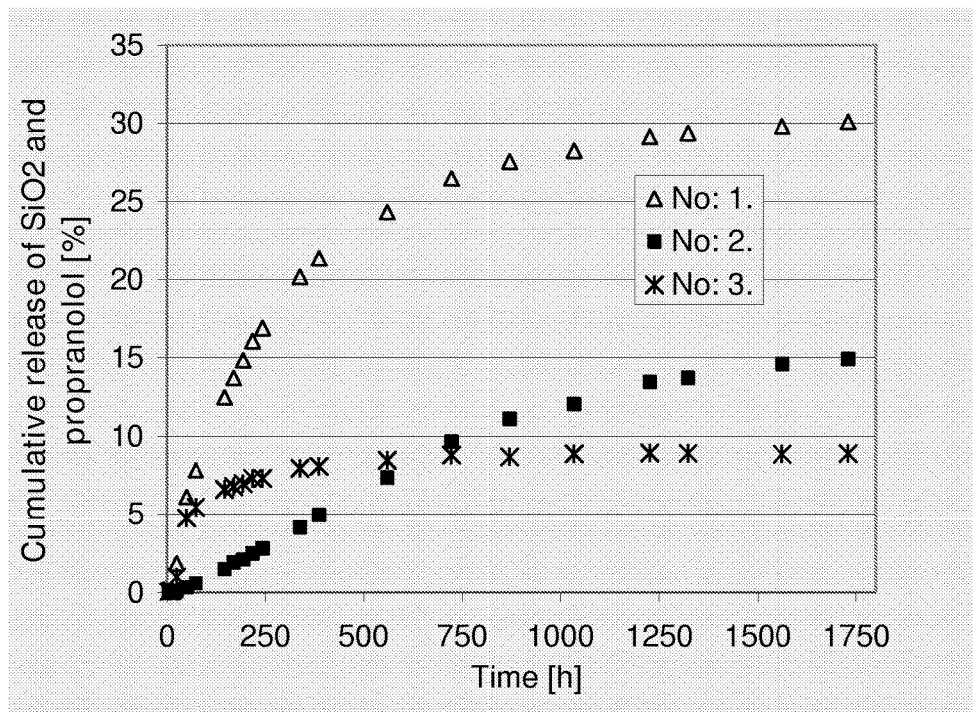
FIG. 3 shows dissolution of propranolol comprising $SiO_2$ monolith matrices according to the invention and release of propranolol from the matrices.

$SiO_2$ monolith dissolution in TRIS, and propranolol release in TRIS and in $SiO_2$ saturated TRIS are presented in FIG. 3.

Curve 1 (FIG. 3)

Cumulative release of propranolol in TRIS solution.

Curve 2 (FIG. 3)

Cumulative dissolution of $SiO_2$ in TRIS solution. The calculated $SiO_2$ dissolution rate was 0.009 wt-%/h.

Curve 3 (FIG. 3)

Cumulative release of propranolol in $SiO_2$ saturated TRIS solution.

Example 4

$SiO_2$ microspheres were prepared in the following way, the initial concentration (mol ratio) and calculated pH were: $H_2O$/TEOS=30, pH 2.8 (HCl was used to adjust the pH). Hydrolysis was done at room temperature. Propranolol (drug) was added into the sol. The amount of propranolol was 5 weight-% of the theoretical $SiO_2$ amount in the sol (1 mol TEOS=1 mol $SiO_2$). Microspheres were prepared by spraying silica sol, with a mini spray dryer (B-191, Büchi Labortechnik AG, Switzerland) within 15 minutes after the adding of propranolol. The following process parameters were used: pump 16%, aspirator 95%, and flow 600 l/h. The temperature of the spray nozzle was 120° C.

Matrix dissolution and propranolol release was studied by immersing silica microspheres in 0.005 M TRIS buffer solution (pH 7.4, 37° C.) in in sink conditions ($SiO_2$<30-130 ppm) and 0.005 M TRIS buffer solution (pH 7.4, 37° C.) saturated with $SiO_2$ ($SiO_2$ 120-130 ppm). TRIS was sterilized at 121° C. before use. Dissolution studies were done in a shaking water bath. In a $SiO_2$ saturated TRIS solution the $SiO_2$ concentration does not increase even if a dissolving silica matrix is placed into the solution. The Si concentration of the TRIS buffer at different time points was measured with a spectrophotometer (UV-1601, Shimadzu) analysing the molybdenum blue complex absorbance at 820 nm. The dissolution of the matrix in TRIS is presented as cumulative dissolution of $SiO_2$ matrix. The total amount (100%) of $SiO_2$ is calculated from the theoretical amount of $SiO_2$ that can be obtained from the sol composition according to the net reaction (1 mol of used alkoxide, TEOS corresponds to 1 mol $SiO_2$). No matrix dissolution was observed in $SiO_2$ saturated TRIS. The propanolol concentration is measured directly with a spectrophotometer at a wavelength of 227 nm. The release of the propranolol in TRIS and in $SiO_2$ saturated TRIS and $SiO_2$ microsphere dissolution are presented as cumulative release in FIG. 4.

Figure 4:
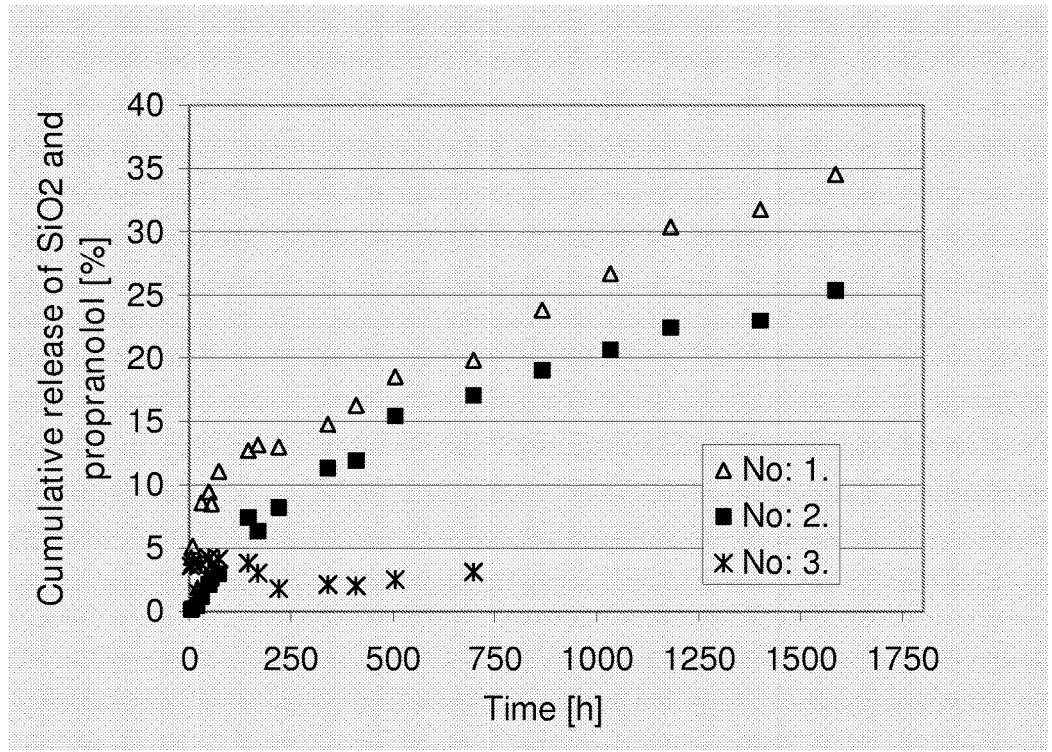
FIG. 4 shows dissolution of propranolol comprising $SiO_2$ microspheres according to the invention and release of propranolol from the microspheres.

Curve 1 (FIG. 4)

Cumulative release of propranolol in TRIS solution.

Curve 2 (FIG. 4)

Cumulative dissolution of $SiO_2$ in TRIS solution. The calculated $SiO_2$ dissolution rate was 0.016 wt-%/h.

Curve 3 (FIG. 4)

Cumulative release of propranolol in $SiO_2$ saturated TRIS solution.

Example 5

$SiO_2$ monoliths were prepared in the following way, the initial concentration (mol ratio) and calculated pH were: $H_2O$/TEOS=30, pH 2 (HCl was used to adjust the pH). Hydrolysis was done at room temperature. The sol was aged and dried simultaneously at 40° C. for 66 hours. After ageing and drying the pH of the sol was adjusted with NaOH to 6.2 and a BSA-water solution (protein) was added into the sol. The amount of BSA was 5 weight-% of the theoretical $SiO_2$ amount in the sol (1 mol TEOS=1 mol $SiO_2$). The $H_2O$/TEOS mol ratio after adding the BSA-water solution was 34. The sol was pipetted into the mould and aged at 4° C. Drying of the gel occurred at 4° C. with free evaporation to the constant weight.

Matrix dissolution and BSA release was studied by immersing silica monoliths in 0.005 M TRIS buffer solution (pH 7.4, 37° C.) in in sink conditions ($SiO_2$<30 ppm). TRIS was sterilized at 121° C. before use. Dissolution studies were done in a shaking water bath. Si concentration of the TRIS at different time points was measured with a spectrophotometer (UV-1601, Shimadzu) analysing the molybdenum blue complex absorbance at 820 nm. Dissolution of the matrix is presented as cumulative release of $SiO_2$. The total amount (100%) of $SiO_2$ is calculated from the theoretical amount of $SiO_2$ that can be obtained from the sol composition according to the net reaction (1 mol of used alkoxide, TEOS corresponds to 1 mol $SiO_2$). BSA concentration was analysed with the fluorescence method (Photo Technology International) with NanoOrange Kit (Molecular Probes).

Figure 5:
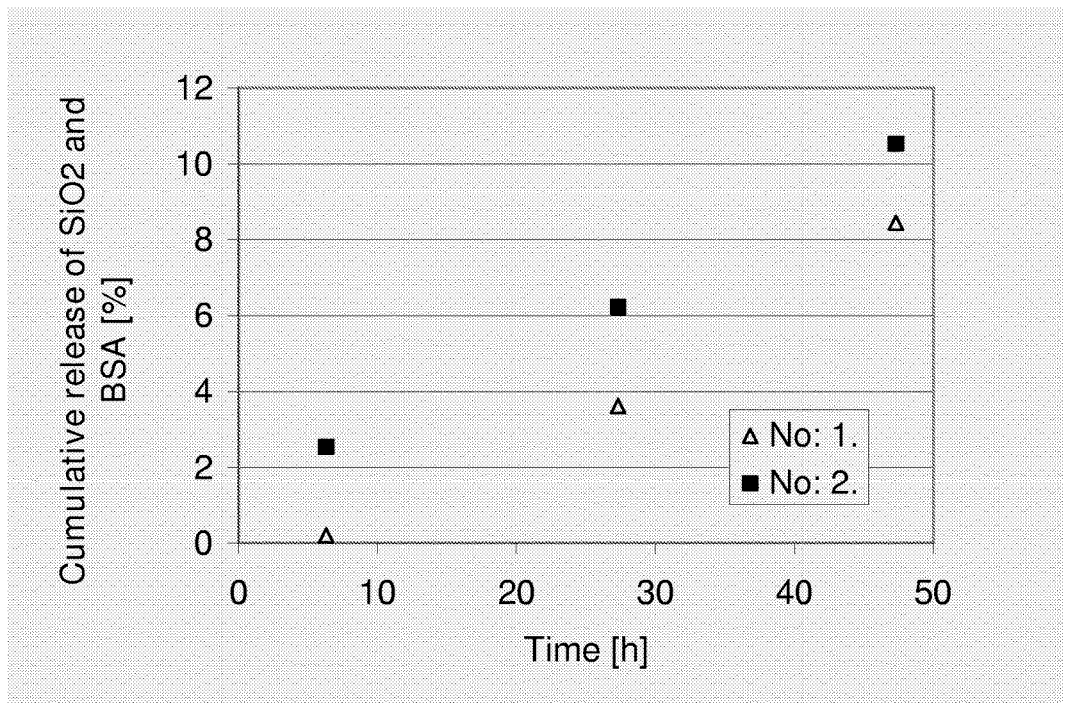
FIG. 5 shows dissolution of BSA (protein) comprising $SiO_2$ monolith matrices according to the invention and release of BSA from the matrices.

$SiO_2$ monolith dissolution and BSA release are presented in FIG. 5.

Curve 1 (FIG. 5)

Cumulative release of BSA in TRIS solution.

Curve 2 (FIG. 5)

Cumulative dissolution of $SiO_2$ in TRIS solution. The calculated $SiO_2$ dissolution rate was 0.196 wt-%/h.

Example 6

$SiO_2$ monoliths are prepared in the following way, the initial concentration (mol ratio) and calculated pH were: $H_2O$/TEOS=22, pH 2.8 (HCl was used to adjust the pH). Hydrolysis of the sol was done at room temperature. pH of the sol was adjusted with 0.5 M NaOH to 5.2 and BSA-water solution (protein) was added into the sol. The amount of BSA was 7 weight-% of the theoretical $SiO_2$ amount in the sol (1 mol TEOS=1 mol $SiO_2$). The $H_2O$/TEOS mol ratio after adding the BSA was 30. The sol was pipetted into the mould and aged at 4° C. for 96 h. Drying of the gel occurred at 4° C. with free evaporation to constant weight.

BSA release was studied by immersing silica monoliths in 0.005 M TRIS buffer solution (pH 7.4, 37° C.) in in sink conditions ($SiO_2$<30 ppm) and 0.005 M TRIS buffer solution (pH 7.4, 37° C.) saturated with $SiO_2$ ($SiO_2$ 120-130 ppm). TRIS was sterilized at 121° C. before use. The release studies were done in the shaking water bath. In $SiO_2$ saturated TRIS solution BSA release is not caused by the matrix dissolution. BSA concentration was measured directly with a spectrophotometer at the wavelength of 220 nm. The release of the BSA in TRIS and in $SiO_2$ saturated TRIS is presented as cumulative release.

Figure 6:
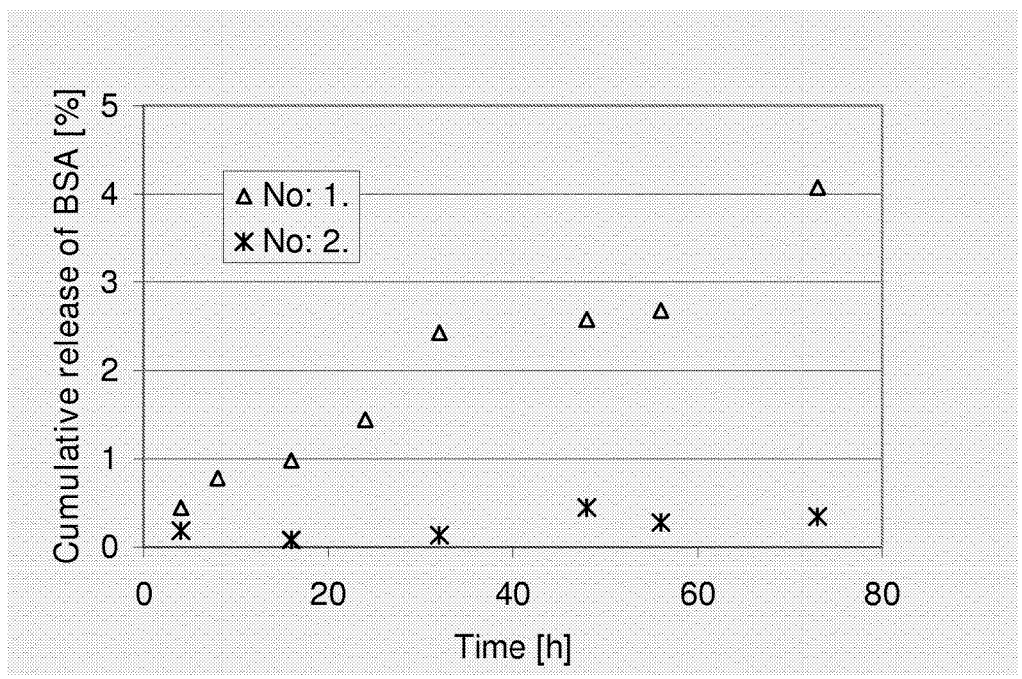
FIG. 6 shows release of BSA (protein) from $SiO_2$ monolith matrices according to the invention.

Release of BSA in TRIS and in $SiO_2$ saturated TRIS is presented in FIG. 6.

Curve 1 (FIG. 6)

Cumulative release of BSA in TRIS solution.

Curve 2 (FIG. 6)

Cumulative release of BSA in $SiO_2$ saturated TRIS solution.

Example 7

$SiO_2$ microspheres are prepared in the following way, the initial concentration (mol ratio) and calculated pH were: $H_2O$/TEOS=22, pH 2.8 (HCl was used to adjust the pH). Hydrolysis was done at room temperature. pH of the sol was adjusted with 0.5 M NaOH to 5.3 and the BSA-water solution was added into the sol. The amount of BSA was 5 weight-% of the theoretical $SiO_2$ amount in the sol (1 mol TEOS=1 mol $SiO_2$). The $H_2O$/TEOS mol ratio after adding the BSA-water solution was 30. Microspheres were prepared by spraying the silica sol with a mini spray dryer (B-191, Büchi Labortechnik AG, Switzerland) within in 15 minutes after pH adjustment to 5.3 and BSA addition. The following process parameters were used: pump 16%, aspirator 95%, and flow 600 l/h. The temperature of the spray nozzle was 120° C.

BSA release was studied by immersing silica microspheres in 0.005 M TRIS buffer solution (pH 7.4, 37° C.) in in sink conditions ($SiO_2$<30 ppm) and 0.005 M TRIS buffer solution (pH 7.4, 37° C.) saturated with $SiO_2$ ($SiO_2$ 120-130 ppm). TRIS was sterilized at 121° C. before use. The release studies were done in a shaking water bath. In the $SiO_2$ saturated TRIS solution BSA release is not caused by the matrix dissolution. BSA concentration was measured directly with spectrophotometer at the wavelength 220 nm. The release of the BSA in TRIS and in $SiO_2$ saturated TRIS is presented as cumulative release.

Figure 7:
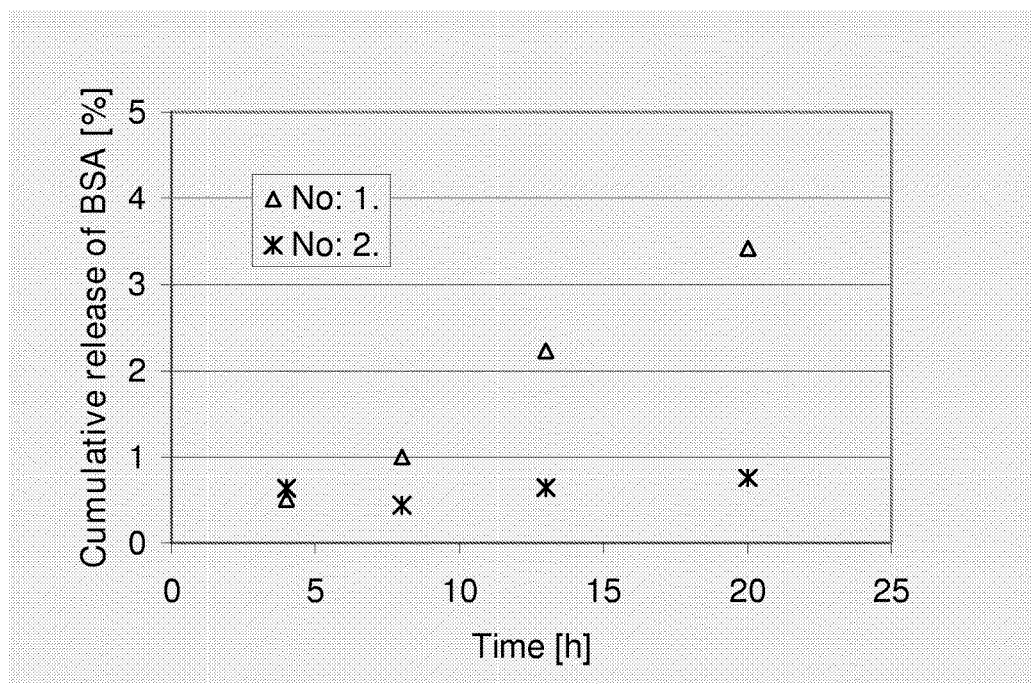
FIG. 7 shows release of BSA (protein) from $SiO_2$ microspheres according to the invention.

Release of BSA in TRIS and in $SiO_2$ saturated TRIS is presented in FIG. 7.

Curve 1 (FIG. 7)

Cumulative release of BSA in TRIS solution.

Curve 2 (FIG. 7)

Cumulative release of BSA in $SiO_2$ saturated TRIS solution.

It will be appreciated that the methods of the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

Example 8

$SiO_2$ monoliths are prepared in the following way, the initial concentration (mol ratio) and calculated pH were: $H_2O$/TEOS=24, pH 2.8 (HCl was used to adjust the pH). Hydrolysis of the sol was done at room temperature. pH of the sol was adjusted with 0.5 M NaOH to 5.0 and BSA-water solution (protein) was added into the sol. The amount of BSA was 5 weight-% of the theoretical $SiO_2$ amount in the sol (1 mol TEOS=1 mol $SiO_2$). The $H_2O$/TEOS mol ratio after adding the BSA was 30. The sol was pipetted into the mould and aged at 4° C. for 96 h. Drying of the gel occurred at 4° C. with free evaporation to constant weight.

BSA release was studied by immersing silica monoliths in 0.005 M TRIS buffer solution (pH 7.4, 37° C.) in in sink conditions ($SiO_2$<30 ppm). TRIS was sterilized at 121° C. before use. The release studies were done in the shaking water bath. BSA concentration was measured directly with a spectrophotometer at the wavelength of 220 nm. The release of the BSA in TRIS is presented as cumulative release.

Figure 8:
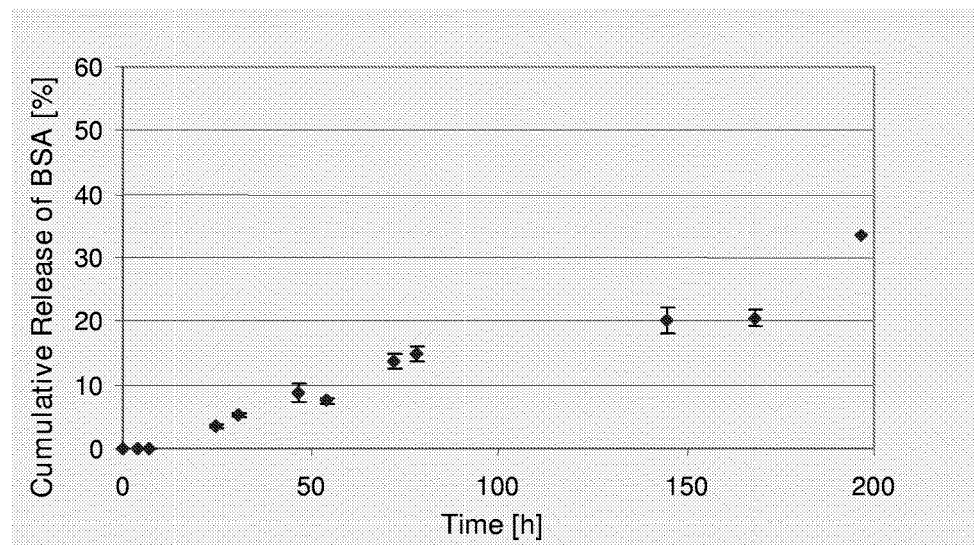
FIG. 8 shows release of BSA (protein) from $SiO_2$ monolith matrices according to the invention.

Release of BSA in TRIS is presented in FIG. 8.

The invention claimed is:

1. A bioresorbable siloxane prepared from tetraethoxysilane, wherein said siloxane is
    a) a monolith having a minimum diameter of ≥0.5 mm and a siloxane dissolution rate in TRIS buffer at a temperature of +37° C. and pH 7.4 of ≥2.0 wt-%/hour, or
    b) a coating having a thickness of <0.5 mm and a siloxane dissolution rate in TRIS buffer at a temperature of +37° C. and pH 7.4 of ≥0.15 wt-%/hour, or
    c) a particle having a maximum diameter of ≤100 μm and a siloxane dissolution rate in TRIS buffer at a temperature of +37° C. and pH 7.4 is ≥1.0 wt-%/hour,
    wherein said siloxane dissolution rate is measured from a linear phase of a dissolution curve.

2. A composition comprising the bioresorbable siloxane of claim 1, and at least one biologically active agent other than the siloxane itself.

3. The composition of claim 2, wherein said at least one biologically active agent is a peptide, protein or cell.

4. The bioresorbable siloxane of claim 1, wherein the siloxane is in the form of a monolith and has a dissolution rate of ≥4.0 wt-%/hour.

5. A bioresorbable siloxane prepared from tetraethoxysilane, wherein
    a) said siloxane is a monolith having a diameter of ≥0.5 mm, and a siloxane dissolution rate in a TRIS buffer at a temperature of +37° C. and pH 7.4 is from 0.001 to 0.05 wt-%/hour, or
    b) said siloxane is a coating having a thickness of <0.5 mm and a siloxane dissolution rate in TRIS buffer at a temperature of +37° C. and pH 7.4 is from 0.001 to 0.05 wt-%/hour,
    wherein said siloxane dissolution rate is measured from a linear phase of a dissolution curve.

6. A composition comprising the bioresorbable siloxane of claim 5, and at least one biologically active agent other than the siloxane itself.

7. The composition of claim 6, wherein said at least one biologically active agent is a peptide, protein or cell.

* * * * *